(12) United States Patent
Earthman et al.

(10) Patent No.: US 11,939,245 B2
(45) Date of Patent: Mar. 26, 2024

(54) ALTERNATING MAGNETIC FIELD SYSTEMS AND METHODS FOR GENERATING NANOBUBBLES

(71) Applicant: THE REGENTS OF THE UNIVERSITY OF CALIFORNIA, Oakland, CA (US)

(72) Inventors: James C. Earthman, Irvine, CA (US); Chuck Wagner, San Diego, CA (US); Ruqian Wu, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 383 days.

(21) Appl. No.: 17/173,499

(22) Filed: Feb. 11, 2021

(65) Prior Publication Data
US 2021/0163321 A1  Jun. 3, 2021

Related U.S. Application Data

(63) Continuation-in-part of application No. 16/160,875, filed on Oct. 15, 2018, now abandoned.
(Continued)

(51) Int. Cl.
C02F 1/48      (2023.01)
A61N 2/00     (2006.01)
C02F 103/02  (2006.01)

(52) U.S. Cl.
CPC .............. *C02F 1/481* (2013.01); *A61N 2/004* (2013.01); *C02F 2103/026* (2013.01); *C02F 2303/08* (2013.01); *C02F 2303/20* (2013.01)

(58) Field of Classification Search
CPC ............. C02F 1/481; C02F 2103/026; C02F 2303/08; C02F 2303/20; C02F 2303/26; A61N 2/004
See application file for complete search history.

(56) References Cited

U.S. PATENT DOCUMENTS 5,453,188 A * 9/1995 Florescu ................. C02F 1/481
                                                        210/695
6,143,171 A * 11/2000 Van Aarsen ......... F02M 27/045
                                                        210/695
(Continued)

FOREIGN PATENT DOCUMENTS

CA   2641822 C    11/2016
DE   9103875 U1 *  7/1992
(Continued)

OTHER PUBLICATIONS

Takahashi, M., 2005, Zeta potential of microbubbles in aqueous solutions: electrical properties of the gas-water Interface, J. Phys. Chem. B 109:21858-21864.
(Continued)

*Primary Examiner* — Waqaas Ali
(74) *Attorney, Agent, or Firm* — NGUYEN TARBET LLC (57) ABSTRACT

Alternating magnetic field (AMF) systems and devices and methods for producing nanobubbles said methods and devices. The AMF systems and devices of the present invention may feature sets of magnets configured to expose a flowing liquid to an alternating magnetic field. The alternating magnetic field destabilizes dissolved gas molecules to produce nanobubbles. The methods, systems, and devices of the present invention may be used to treat solution, for reducing fouling or corrosion in a tube system or pipe system, methods for increasing water porosity of soil, methods for treating thromboembolic disease, etc.

20 Claims, 5 Drawing Sheets
(5 of 5 Drawing Sheet(s) Filed in Color)

Related U.S. Application Data (60) Provisional application No. 62/572,216, filed on Oct. 13, 2017.

(56) References Cited

U.S. PATENT DOCUMENTS

| | | | |
|---|---|---|---|
| 6,709,490 | B1 | 3/2004 | De Los Santos |
| 7,632,400 | B2 | 12/2009 | Yamasaki et al. |
| 7,767,081 | B2 * | 8/2010 | Meeks ................. F02M 27/045 |
| | | | 210/695 |
| 7,803,272 | B2 | 9/2010 | Yamasaki et al. |
| 7,914,677 | B2 | 3/2011 | Yamasaki et al. |
| 2012/0067802 | A1 * | 3/2012 | Irvin ..................... B03C 1/0332 |
| | | | 210/222 |

FOREIGN PATENT DOCUMENTS

| | | |
|---|---|---|
| DE | 102007037186 B3 | 10/2008 |
| EP | 0119368 A1 | 9/1984 |
| EP | 0 237 935 B1 | 9/1990 |
| JP | 2015-188857 A | 11/2015 |

OTHER PUBLICATIONS

What is Atherosclerosis? National Heart, Lung, and Blood Institute. NIH, Jul. 1, 2011. Web. Sep. 20, 2014. <http://www.nhlbi.nih.gov/health/health-topics/topics/atherosclerosis/>.

Mayo Clinic Staff ".Statin Side Effects: Weigh the Benefits and Risks." http://www.mayoclinic.com/health/statin-side-effects/MY00205. Accessed Dec. 2013.

"Crestor Lawsuit" http://lawsuits.lawinfo.com/Crestor/index.html. Accessed Dec. 2013.

M. Ast M.D., W. H. Frishman M.D., Bile Acid Sequestrants, The Journal of Clinical Pharmacology, vol. 30, No. 2, pp. 99-105, Mar. 2013.

H. R. Davis, E. P. Veltri, Zetia: Inhibition of Niemann-Pick C1 Like 1 (NPC1L1) to Reduce Intestinal Cholesterol Absorption and Treat Hyperlipidemia, Journal of Atherosclerosis and Thrombosis, vol. 14, No. 3, p. 101, 2007.

I. Otsuka, S. Ozeki, Does Magnetic Treatment of Water Change its Properites, The Journal of Physical Chemstry B Letters, vol. 110, pp. 1509-1512, Jan. 2006.

J. Earthman, W. Dang Alternating Magnetic Field Treatment of Service Water to Control Pitting Induced by Sulphate Reducing Bacteria, Corrosion Management, No. 96, pp. 11-14, Jul./Aug. 2012.

M. Switkes, J.W. Ruberti, Rapid Cryofixation/Freeze Fracture for the Study of Nanobubbles at Solid-Liquid Interfaces, Applied Physics Letters, vol. 84, No. 23, pp. 4759-4761, Jun. 2004.

P. Attard M. Moody, J. Tyrrell, Nanobubbles: the big picture, Physica A, vol. 314, pp. 696-705, 2002.

S. Yang, P. Harmsma, J. Pozo, M. Yousefi, Detection of Nanobubble Generation and Stability by a SOI Nanophotonic Ring Resonator, The European Conference on Lasers and Electro-Optics Munich Germany, May 2011.

D. R. Meeker, H. D. Kesten, Composition of Pathological Calcium Deposits, Journal of Biological Chemistry vol. 113, pp. 289-296, Nov. 1936.

P. E. Vincent, A. M. Plata, A. A. E. Hunt, P. D. Weinberg, and S. J. Sherwin. Blood Flow in the Rabbit Aortic Arch and Descending Thoracic Aorta. Journal of The Royal Society Interface vol. 8, No. 65, pp. 1708-1719, Dec. 2011.

International Search Report Issued for PCT Application No. PCT/US18/55932 dated Jan. 9, 2019.

\* cited by examiner

ALTERNATING MAGNETIC FIELD SYSTEMS AND METHODS FOR GENERATING NANOBUBBLES

CROSS REFERENCE

This application is a continuation-in-part and claims benefit to U.S. patent application Ser. No. 16/160,875 filed Oct. 15, 2018, which claims benefit to U.S. Provisional Patent Application No. 62/572,216 filed Oct. 13, 2017, the specifications of which are incorporated herein in their entirety by reference.

FIELD OF THE INVENTION

The present invention relates to nanobubbles, more particularly to the production of nanobubbles using an alternating magnetic field (AMF) system.

BACKGROUND OF THE INVENTION

Nanobubbles are typically produced in water using gas infusion methods and ultrasonic excitation methods. However, these approaches require relatively high external power inputs to produce an effective concentration of nanobubbles. It was surprisingly discovered that gas dissolved in water could be destabilized by a rapidly changing magnetic field that in turn leads to precipitation of nanoscale oxygen gas bubbles (nanobubbles).

The present invention features alternating magnetic field (AMF) systems and devices as well as methods for producing nanobubbles using the AMF systems and devices of the present invention. The present invention also features applications of the AMF systems and devices and the AMF-generated nanobubbles.

The AMF systems of the present invention may feature neodymium magnets and/or other appropriate magnets. Without wishing to limit the present invention to any theory or mechanism, it is believed that the magnets (e.g., neodymium, others, or combinations thereof) used in the present invention are advantageous over those typically used in other systems because they have higher Gauss readings. For example, other systems that use only ferrite magnets may not be able to achieve the same results as what has been shown in the experiments herein.

The AMF methods, systems, and devices of the present invention have a low energy requirement. For example, as compared to the gas infusion and ultrasonic excitation methods for producing nanobubbles, the methods and systems of the present invention require less power input to produce an effective concentration of nanobubbles. The methods and systems of the present invention are also easy to use and may be used for a broad range of applications.

AMF treated solutions containing nanobubbles may be used to reduce fouling and corrosion in tubing and pipe systems that deliver liquids from one location to another (e.g., purification systems, desalination facilities, cooling water systems, etc.). Another application includes increasing efficiency of irrigation (e.g., increasing solution uptake during irrigation of plants). For example, AMF treated solutions containing nanobubbles may be used in irrigation lines to break down calcium carbonate and other compounds in soils. This can lead to an increase in soil porosity that allows plants to up take up more water and gases transferred to their roots with less irrigation. In addition, the methods and systems of the present invention may be used for intravascular treatments for thromboembolic disease. The nanobubbles produced by AMF can also assist in wound healing. The present invention is not limited to the aforementioned applications.

SUMMARY OF THE INVENTION

The present invention features alternating magnetic field (AMF) systems and methods for producing nanobubbles and applications of the AMF-generated nanobubbles.

For example, the present invention features alternating magnetic field (AMF) systems for producing nanobubbles. In some embodiments, the nanobubbles comprise nanoscale gas bubbles (e.g., oxygen bubbles). In some embodiments, the AMF system comprises one or more sets of magnets configured to expose a flowing liquid to an alternating magnetic field. For example, in some embodiments, the AMF system comprise a pipe with a core mounted within the pipe, wherein the core extends along a length of the pipe while allowing liquid to flow through the pipe. For example, in certain embodiments, the magnets extend from a first end of the core to a second end of the core. A plurality of magnets is housed in the core, wherein the magnets are positioned north end-to-north end and south end-to-south end. The magnets expose a flowing liquid to an alternating magnetic field.

In some embodiments, the magnets comprise neodymium magnets. In some embodiments, the magnets comprise ferrite magnets. In some embodiments, the magnets comprise a combination of different types of magnets. For example, in some embodiments, the magnets comprise neodymium magnets and another type of magnet.

In some embodiments, the AMF system comprises a tube for allowing liquid to flow from a first end to a second end, the tube comprises a set of magnets. In some embodiments, the magnets extend from the first end to the second end of the tube. In other embodiments, the alternating magnetic field can be induced by an electro-magnetic or series of electromagnets powered by an alternating electrical current. For these embodiments, the liquid can be flowing or static in a container within the coil of the electromagnet.

The present invention also features methods for producing nanobubbles. In some embodiments, the method comprises subjecting a solution to an alternating magnetic field (AMF) system according to the present invention, wherein the AMF system destabilizes dissolved gas molecules in the solution to precipitate nanobubbles comprising the gas molecules (e.g., oxygen molecules). Referring to all of the methods and systems disclosed herein, in some embodiments, the solution comprises calcium, carbonate, ions that can produce calcium bearing compounds, sodium chloride, selenium ions or other ions, the like, or a combination thereof.

The present invention also features methods of treating a solution. In some embodiments, the method comprises subjecting the solution to an alternating magnetic field (AMF) system according to the present invention, wherein the AMF system generates nanobubbles. The nanobubbles may bind or cluster nanoparticles in the solution. In some embodiments, the nanobubbles function to deliver gas to the solution.

The present invention also features methods of reducing fouling or corrosion in a tube or pipe system with flowing liquid. In some embodiments, the method comprises using an alternating magnetic field (AMF) system according to the present invention to produce nanobubbles and introducing the nanobubbles to the liquid in the tube or pipe system. The nanobubbles may bind or cluster nanoparticles in the solution so the nanoparticles do not foul or corrode the tube or pipe system. In some embodiments, introducing the nanobubbles to the liquid in the tube or pipe system comprises in-line introduction of liquid flowing through the tube or pipe system.

The present invention also features methods of increasing water porosity of soil. In some embodiments, the method comprises using an alternating magnetic field (AMF) system according to the present invention to produce nanobubbles and introducing the nanobubbles to liquid flowing through an irrigation line in the soil. The nanobubbles may lead to the breakdown and/or dissolution of compounds in the soil to increase water porosity of the soil. In some embodiments, the compound comprises calcium carbonate.

The present invention also features methods of treating thromboembolic disease in a patient. In some embodiments, the method comprises using an alternating magnetic field (AMF) system according to the present invention to produce nanobubbles and introducing the nanobubbles to blood in a vessel the patient. The nanobubbles may bind or cluster nanoparticles in the blood. In some embodiments, the binding or clustering of nanoparticles in the blood leads to a reduction in deposits on walls of the vessel. In some embodiments, the nanobubbles function to deliver gas to the blood in the vessel of the patient.

The present invention also features methods of treating atherosclerosis disease in a patient. In some embodiments, the method comprises using an alternating magnetic field (AMF) system according to the present invention to produce nanobubbles and introducing the nanobubbles to blood in a vessel the patient. The nanobubbles may bind or cluster nanoparticles in the blood. In some embodiments, the binding or clustering of nanoparticles in the blood leads to a reduction in deposits on walls of the vessels. In some embodiments, the nanobubbles function to deliver gas to the blood in the vessel of the patient.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which.

DETAILED DESCRIPTION OF THE INVENTION

The present invention features alternating magnetic field (AMF) systems and devices, methods for producing nanobubbles using the AMF systems and devices of the present invention, and applications of the AMF systems and devices and AMF-generated nanobubbles.

Figure 1:
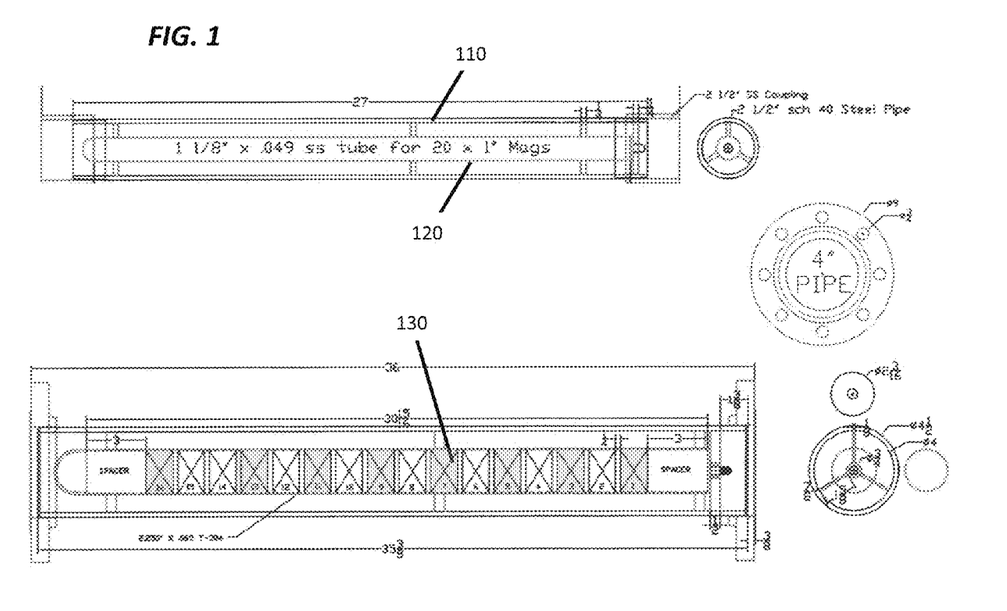
FIG. 1 shows a schematic drawing of an embodiment of the system of the present invention.

FIG. 1 shows schematic views of an AMF system (100) of the present invention. The system (100) comprises sets of permanent magnets configured in such a way as to expose a flowing liquid to an alternating magnetic field (AMF). The liquid flows through a pipe (110) containing a core (120) of permanent magnets (130) positioned North end-to-North end and South end to South end as shown in the embodiment machine drawing in FIG. 1. The core (120) is mounted inside the pipe (110). Note the present invention is not limited to the dimensions shown in FIG. 1.

In some embodiments, the core (120) of the AMF system (100) is enclosed, such that the liquid flowing through the pipe (110) flows around the core (120) without entering the core (120). As a non-limiting example, the core (120) may be a naturally airtight capsule, i.e. an ellipsoid manufactured to contain the permanent magnets (130) while remaining airtight. As another non-limiting example, the core (120) may be a capsule with an opening that is plugged up in a manner that makes the core (120) airtight, i.e. an ellipsoid containing the permanent magnets (130) with a small hole on a first end, such that the small hole is plugged by a peg to seal the core (120) (see FIGS. 1-2). The enclosed core (120) of the present invention may be capable of forcing the flow of liquid directed through the presently claimed invention to the spaced between the core and the pipe. The space between the core and the pipe is the most even and controlled space and therefore allows for the most effective generation of nanobubbles through the use of magnetic fields.

In some embodiments, the core (120) of the AMF system (100) is shaped such that the liquid flows straight through the pipe (110). The shape of the core (120) may be a cylinder or ellipsoid, wherein the face making up the circumference of the core (120) matches an inner shape of the pipe (110) (see FIGS. 1-2). In some embodiments, there may exist a proportionally large space between the outer surface of the core (120) and the inner surface of the pipe (110). The size of the space between the core (120) and the pipe (110) is determined by a ratio of the outer diameter of the core (120) and the inner diameter of the pipe (110). A lower ratio results in a larger space between the core (120) and the pipe (110), and vice versa. In some embodiments, the ratio may be 1:3 to 35:64. In some embodiments, the ratio may be 35:64 or lower (see FIGS. 1-2). The straight shape of the core (120) combined with the large space between the core (120) and the pipe (110) may allow for the optimal generation of nanobubbles in a liquid directed through said space between the pipe (110) and the core (120). The large space and the straight-shaped core (120) allow for a high flow rate of liquid within the AMF system (100), which was found to be optimal in the efficient generation of nanobubbles when compared to smaller spaced and lower flow rates through experimental trials carried out by the inventors.

Without wishing to limit the present invention to any theory or mechanism, an advantage of AMF production of nanobubbles with permanent magnets is that it does not necessarily require external power input other than what is needed to move the liquid from one location to another. In other words, all of the energy used by the system is provided by the flow (e.g., kinetic energy) of the liquid through the system. Without wishing to limit the present invention to any theory or mechanism, energy harvested from the flowing liquid does not significantly increase the power required to pump the liquid through a piping or irrigation system. All other known methods are believed to require an additional external power source to produce nanobubbles.

Figure 2:
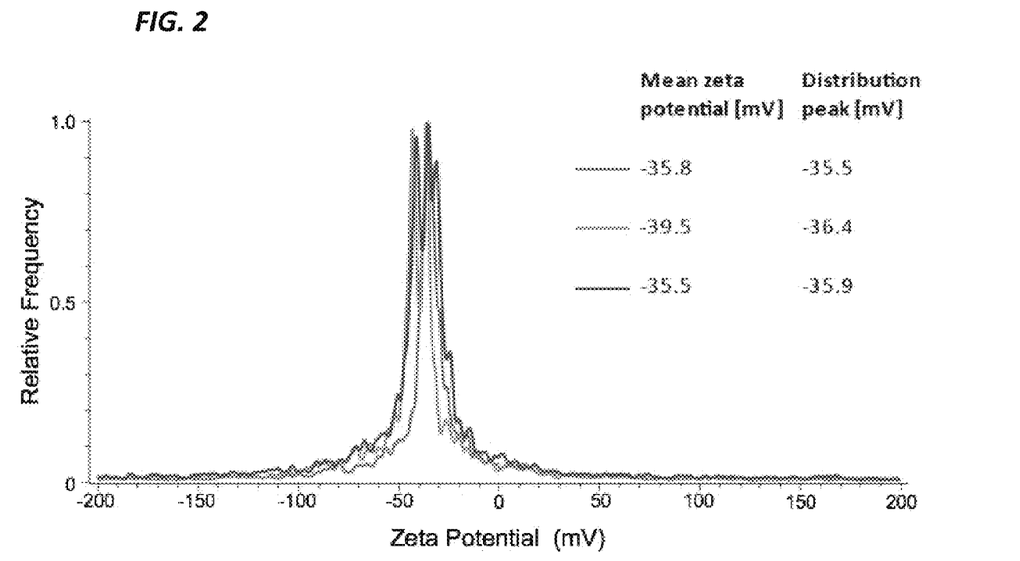
FIG. 2 shows Zeta potential data for three replicates of deionized water treated with an AMF system of the present invention, indicating the presence of nanobubbles.

Nanobubble generation was confirmed with the measurement of zeta potential for three replicate samples of deionized water treated with an AMF system of the present invention. Zeta potential is to a physical property exhibited by a particle in suspension and is a measurement of the magnitude of the electrostatic repulsion or attraction between particles and bubbles. The zeta potential of nanobubbles in neutral pH water at room temperature generally falls between −30 and −40 mV as a result of ions concentrated on the bubble surface (see Takahashi, M., 2005, Zeta potential of microbubbles in aqueous solutions: electrical properties of the gas-water interface, *J. Phys. Chem.* B 109:21858-21864). FIG. 2 shows Zeta potential data for three replicates of deionized water treated with an AMF system of the present invention, indicating the presence of nanobubbles. The average zeta potential measured was about −37 V.

Figure 3:
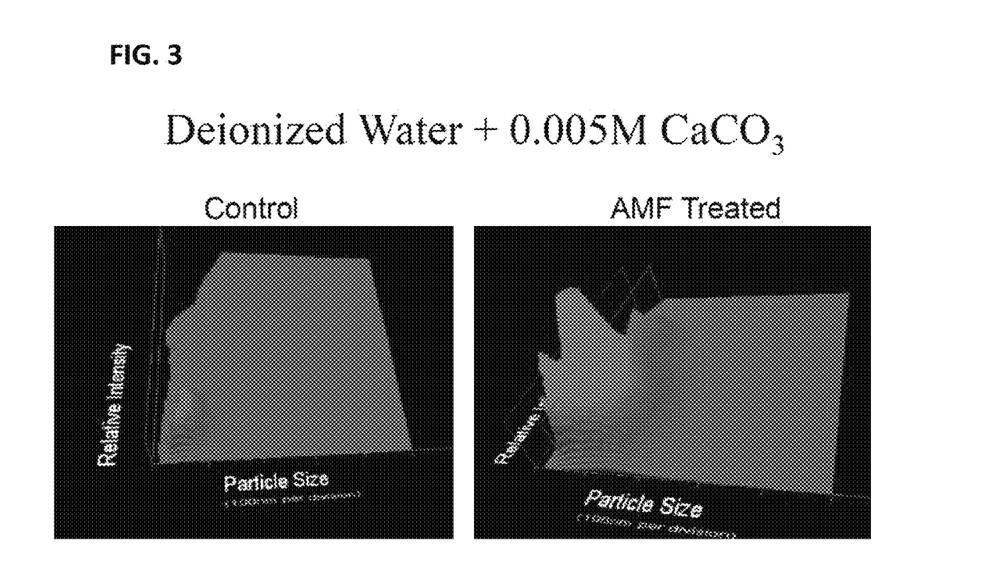
FIG. 3 shows Nanosight results (for measuring nanoparticle size and relative intensity) of deionized water containing 0.005M $CaCO_3$ either untreated or treated with an AMF system of the present invention. Results indicated only one relatively small particle size and relative light intensity for the untreated water and multiple particle sizes and relative intensities for the AMF treated water, indicating the presence of nanobubbles in the AMF treated water in addition to calcium carbonate.
Figure 4:
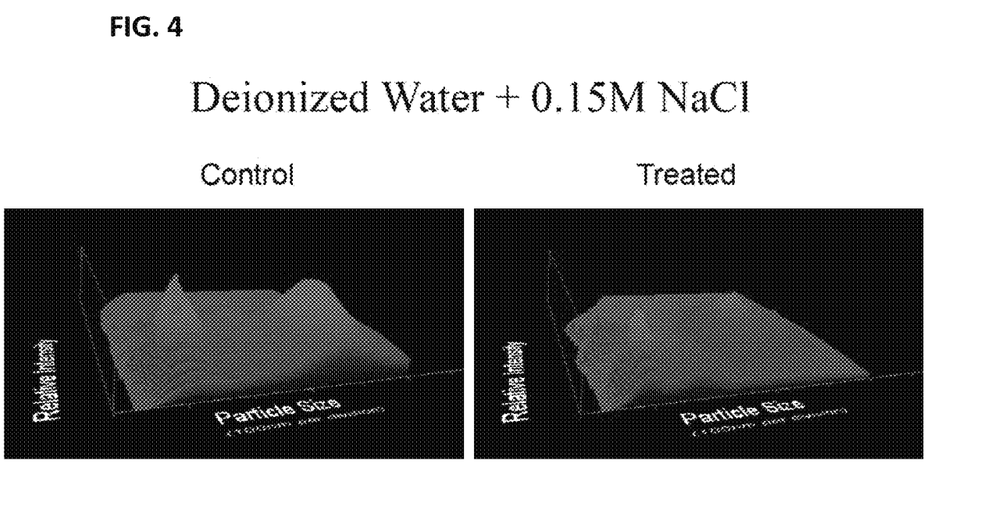
FIG. 4 shows results of Nanosight measurements (for measuring nanoparticle size and relative intensity) for deionized water containing 0.15 M sodium chloride either untreated or treated with an AMF system of the present invention. The partition of the results confirmed the presence of nanobubbles by a shift in relative intensity for the AMF treated sample.

Nanobubbles can be formed in liquids when either calcium carbonate or sodium chloride is present in the water (see FIG. 3, FIG. 4). FIG. 3 shows Nanosight results (for measuring nanoparticle size and relative intensity) of deionized water containing 0.005M CaCO3 either untreated or treated with an AMF system of the present invention. Results indicated only one relatively small particle size and relative light intensity for the untreated water and multiple particle sizes and relative intensities for the AMF treated water, indicating the presence of nanobubbles in the AMF treated water in addition to calcium carbonate. FIG. 4 shows results of Nanosight measurements (for measuring nanoparticle size and relative intensity) for deionized water containing 0.15 M sodium chloride either untreated or treated with an AMF system of the present invention. These results confirmed the presence of nanobubbles by a shift in relative intensity for the treated sample.

EXAMPLE

The following Example describes the dissolution of arterial plaque in an ex vivo rabbit model by administering Ringer's solution treated with an alternating magnetic field (AMF) system of the present invention. The present invention is not limited to the methods, compositions, and systems in this example.

Introduction

Plaque deposits on the inner walls of human arteries, known as atherosclerosis, is the primary contributor to coronary heart disease, carotid artery disease, and peripheral arterial disease. The classes of medications currently used to reduce plaque deposits in the arteries are statins, bile-acid sequestrants, and cholesterol absorption inhibitors. These drugs have been used for a number of years and are effective, but they have notable side effects and drawbacks. Statins have been associated with the significant side effects of severe muscle pain, liver damage, and digestive problems. The statin "Creston" was under threat of being recalled due to cases of significant muscle damage and kidney failure. Bile-acid sequestrants have been linked with a tendency to cause muscle pain, digestive problems, and, on rare occasions, gastrointestinal irritation and bleeding. Conversely, cholesterol absorption inhibitors are associated with much milder side effects than the other classes of plaque-reducing agents. The main drawback of cholesterol absorption inhibitors is their lack of efficacy in removing preexisting calcified plaque. Cholesterol absorption inhibitors prevent new plaque from forming and let the body's natural processes break down preexisting plaque deposits. This process of plaque reduction tends to take a much longer time than that of agents in the other classes and is not very effective for advanced cases of atherosclerosis. In addition to these pharmacological methods, arterial plaque can be removed through surgical procedures. These procedures are highly effective, but invasive and potentially dangerous. In the carotid endarterectomy procedure, the carotid artery is sliced open and the plaque inside is scraped out. This effectively removes plaque but does nothing to prevent it from reoccurring.

Calcium carbonate is a common byproduct of exposure to aqueous solutions and tends to precipitate into a strong solid and collect on the walls of pipes in service water systems. It, along with calcium phosphate, can also be a major component of calcified cardiovascular plaques. These deposits have proven very difficult to remove and have caused significant problems. The following example investigates whether exposing calcified arterial plaque to a common intravenous solution treated with alternating magnetic fields (AMF) can reproducibly cause the plaque to break down or dissolve in ex vivo aorta specimens.

Methods

Figure 5:
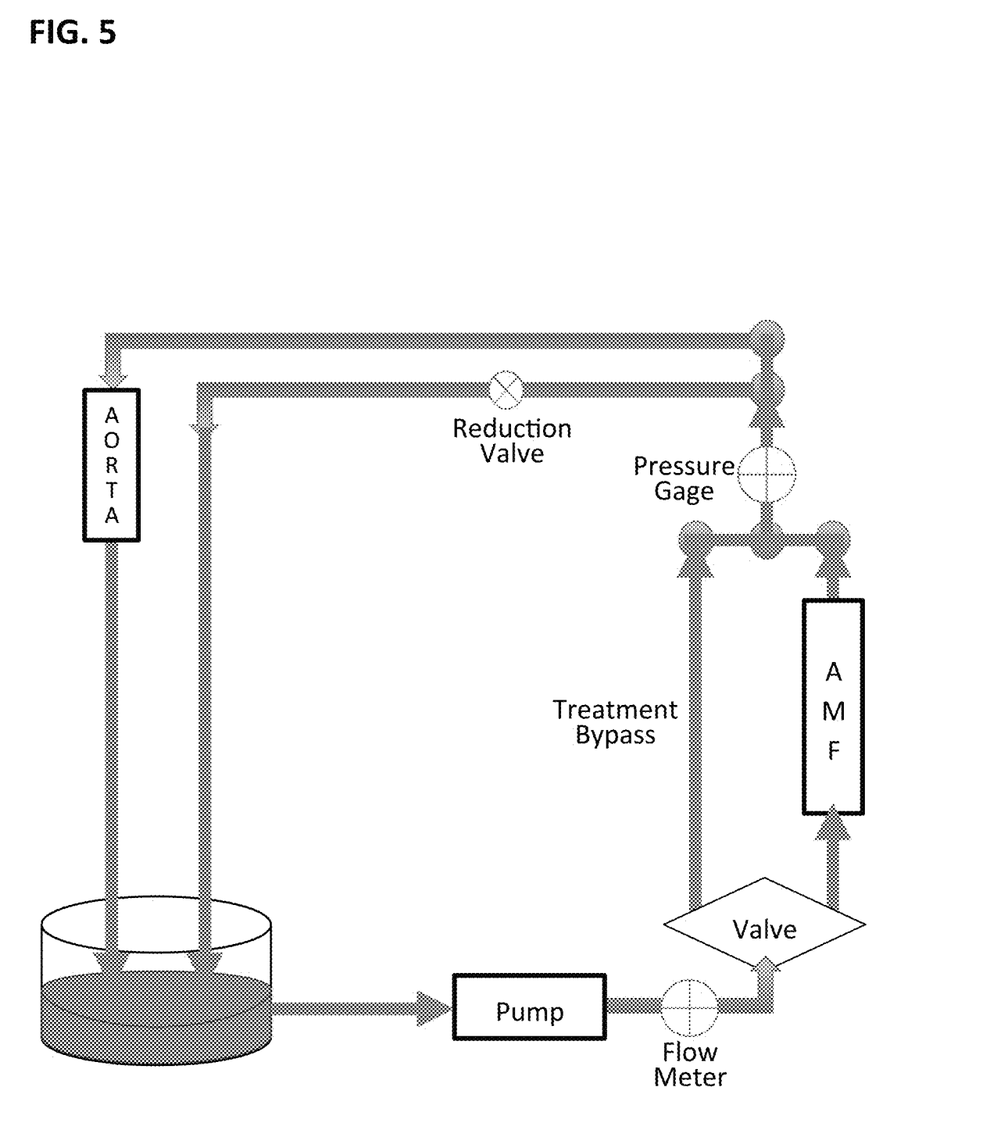
FIG. 5 shows a schematic view of an embodiment of an AMF system.

Experimental System: A continuous flow system was developed to accommodate an alternating magnetic field (AMF) device (Aqua-PhyD Inc., Irvine, CA) used to treat Ringer's solution that was then passed through rabbit descending aorta segments. This system is depicted schematically in FIG. 5. As illustrated in this figure, the experimental system consists of a flow loop made of 9.5 mm ID Tygon tubing that contained approximately 375 mL of Ringer's solution at all times and a 1 L capacity reservoir that initially contained 125 mL of solution. The Ringer's solution was pumped through the system using a Flojet LF122202 1.0 GPM pump (Flojet/Jabsco, Irvine, CA). An F-44500LE-6 Polysulfone Molded flowmeter (Blue-White Industries Ltd., Huntington Beach, CA) was used to measure flow rate. A two-way valve was used to direct the flow either through the AMF device or through a bypass for control testing. A two-way joint was used to divert some of the flow into 3 mm ID silicone tubing while allowing most of the flow to continue through a Tygon tubing bypass. A pinch valve was placed on the Tygon tubing after the adapter to control the pressure and the amount of flow in each branch of the system. The Tygon tubing run-off path then led back to the fluid reservoir, completing the continuous flow loop. The 3 mm diameter silicone tubing led to a small-flow, FLO-RITE GS10810 flowmeter (Key Instruments, Trevose, PA) that also possessed a needle valve to control the maximum flow rate through a rabbit descending aorta specimen (see FIG. 5). The silicone tubing connected to a 3.2 mm ID 304 stainless steel tube. A manometer was situated horizontally to allow for easy determination of pressure in the silicone tubing. Finally, the stainless-steel tube led to a rabbit descending aorta segment, which hung vertically down over the reservoir.

The system was originally tested and refined using rabbit descending aortas that did not contain plaque (obtained from Sierra for Medical Science (Whittier, CA)). These rabbit descending aortas were employed with the surrounding rabbit tissue still attached to help reduce the flow through intercostal side branches. The use of these specimens facilitated the development of a capability to test aorta samples under physiologically relevant levels of flow rate and pressure prior to testing plaque-containing aorta samples.

Rabbit descending aorta segments containing plaque came from a New Zealand White rabbit that was fed a specific diet to promote plaque formation. After 3 months, each descending aorta was harvested from the rabbit and then treated with formaldehyde and stored at 4° C. until Jun. 2014. Pre-treatment images of the inside of one of the aorta segments were obtained using optical coherence tomography (OCT). Following this examination, a 1.5 cm long segment of the rabbit aorta containing plaque was placed in the present flow-loop system for testing. The aorta segments containing plaque were stored in a sealed plastic bottle inside in a cold room held at 6° C.

Test Protocol: Each descending aorta specimen was attached to a stainless-steel inlet tube by sliding it 2-3 mm over the end of the tube and tying black heavy thread around the aorta segment 3-4 times. A knot was also tied around a strap that held the tubing over the reservoir to further secure the aorta segment so that it would not slip during testing. Suspending the stainless-steel tube vertically assured that the rabbit descending aorta contained no kinks or bends. At the beginning of each experiment, Ringer's solution first flowed through the tubing system with the pinch valve and needle valve completely open so there was no pressure forcing fluid through the aorta segment. Then the pinch valve was slowly closed until the small-flow flowmeter read 6.1 mL/s. The needle valve was then quickly closed to reduce the flow rate in the small-flow flowmeter to 2.55 mL/s. This flow rate was chosen because it is approximately equal to the average blood flow rate in the descending aorta for a New Zealand white rabbit.

Two New Zealand white rabbit descending aorta segments containing plaque were tested with AMF treated Ringer's solution once the system was tested with rabbit aorta without plaque. The first sample (Aorta Specimen #1) was a 4 mm long rabbit descending aorta segment containing plaque. A control portion of the experiment was first run for three hours, in which the AMF system was bypassed, so that only untreated Ringer's solution passed through the aorta specimen. This portion of the experiment was then followed by a treatment test for another three hours where the AMF system was brought in line with the flow through the aorta sample.

Approximately 500 mL of Ringer's solution circulated through the tubing system at all times (375 mL in the tubing and 125 mL in the reservoir). After activating the pump, it was necessary to flush out air bubbles that collected in the manometer. This procedure was accomplished by reducing the flow in the small-flow flowmeter, using the needle valve, to nearly 0 mL/s so no fluid was in the manometer and all the air bubbles passed out of the system through the rabbit descending aorta segment. The needle valve was then slowly re-opened until the flow rate reached 2.20 mL/s, slightly below the previously stated target of 2.55 mL/s. The pressure was held constant at a value of approximately 1 kPa during the entire three-hour experiment by periodically making slight adjustments with the needle valve on the small-flow flowmeter. The flow rate through the aorta specimen was recorded at 600 s intervals.

The flow pump was stopped after the three-hour control portion of the experiment and the two-way valve was switched to pass the flow of Ringer's solution through the AMF system so that treated solution would pass through the rabbit aorta specimen containing plaque. The aorta specimen was not touched or removed during this process nor were any other parts of the experimental apparatus. The pump was then reactivated and the treatment portion of the experiment was run for another three hours. The same method for removing air bubbles in the manometer was used for the treatment test as was used for the control portion of the experiment. Once the same flow pressure was reached, it was observed that the initial flow rate was the same as the flow rate observed during the control portion of the experiment. The pressure was again maintained at the same constant value as that for the control test. The flow rate in the aorta specimen was recorded every 600 s. After the three-hour AMF treatment portion of the experiment was completed, the aorta specimen containing plaque was removed from the system and held in a closed container at 6° C.

A second aorta segment containing plaque (Aorta Specimen #2) was weighed prior to flow testing, after the control portion of the experiment and after the AMF treatment part of the test. Aorta Specimen #2 was otherwise tested in a manner identical to that for Aorta Specimen #1. Post-treatment images of the Aorta Specimen #2 were acquired using a dedicated OCT imaging probe for comparison to the pre-treatment images.

Results

Figure 6:
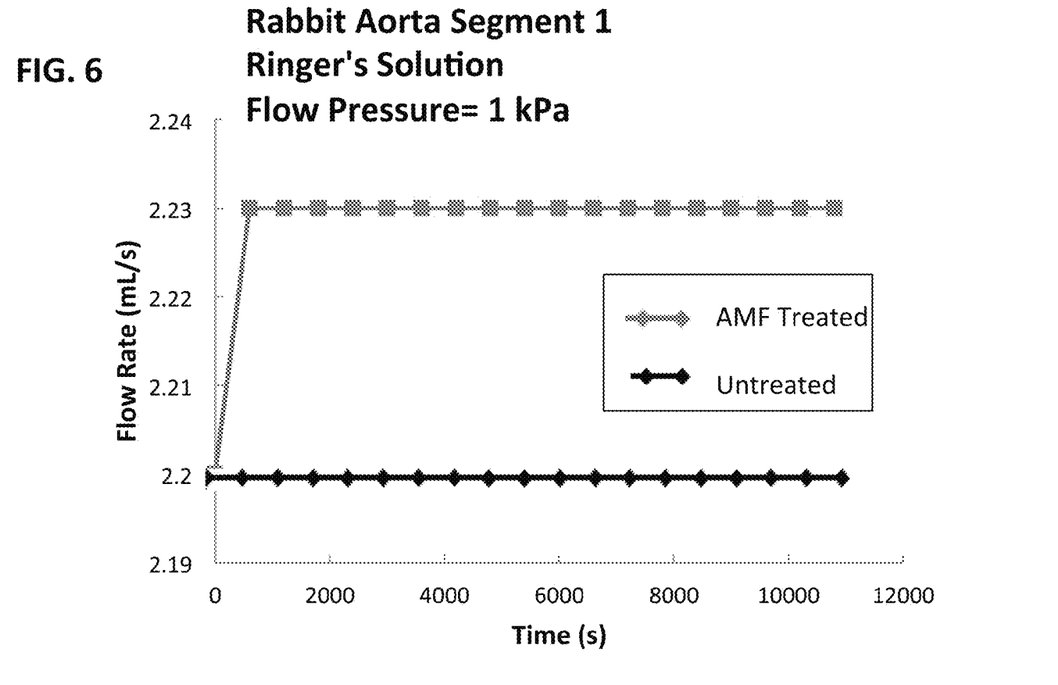
FIG. 6 shows flow rate as a function of time for untreated and AMF treated Ringers solution through rabbit descending aorta specimen 1 containing plaque. The test with untreated Ringers solution was performed first.
Figure 7:
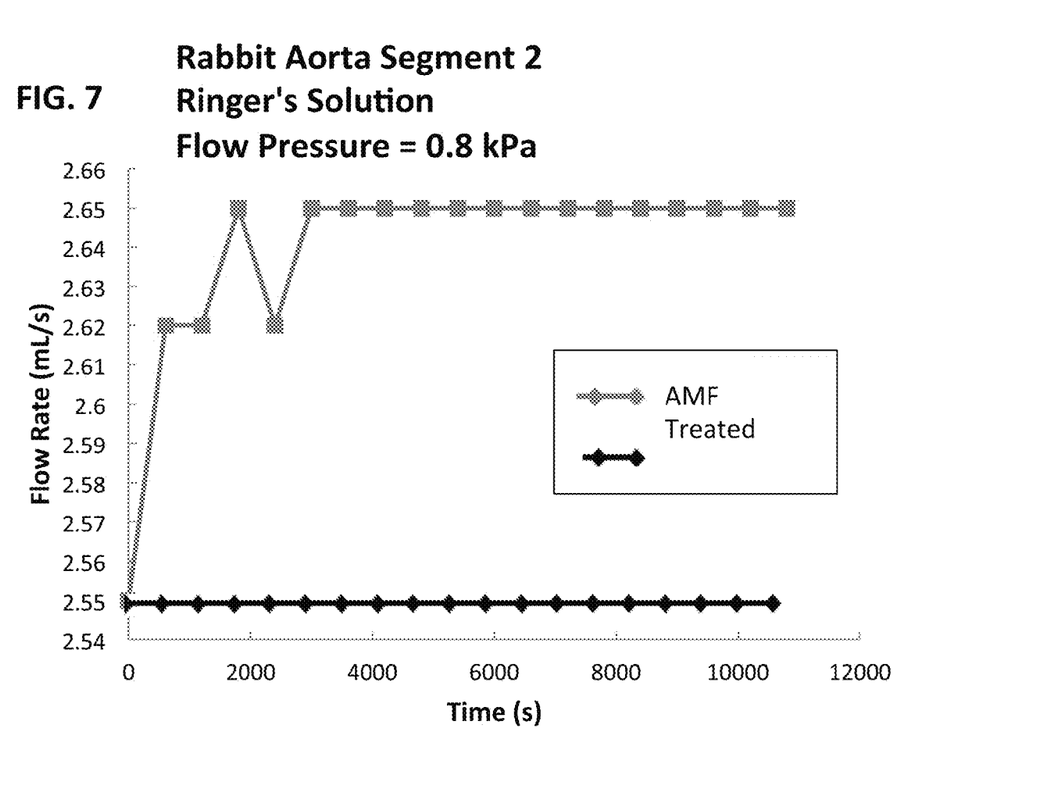
FIG. 7 shows flow rate as a function of time for untreated and AMF treated Ringers solution through rabbit descending aorta specimen 2 containing plaque. The test with untreated Ringers solution was performed first.

Flow Test Data: The control test flow rate data for Aorta Specimen #1 are shown as a function of time in FIG. 6. These data indicate that the flow rate remained constant at 2.20 mL/s+/−0.02 mL/s. FIG. 7 shows corresponding data for Aorta Specimen #1 under AMF treatment conditions. This portion of the experiment began at the same pressure and flow rate as the control test that just ended. However, flow rate rose to 2.23 mL/s during the course of the first 600 s. After this increase within the first 600 s, the flow rate entering the aorta specimen remained constant for the remainder of the three-hour test.

Figure 8:
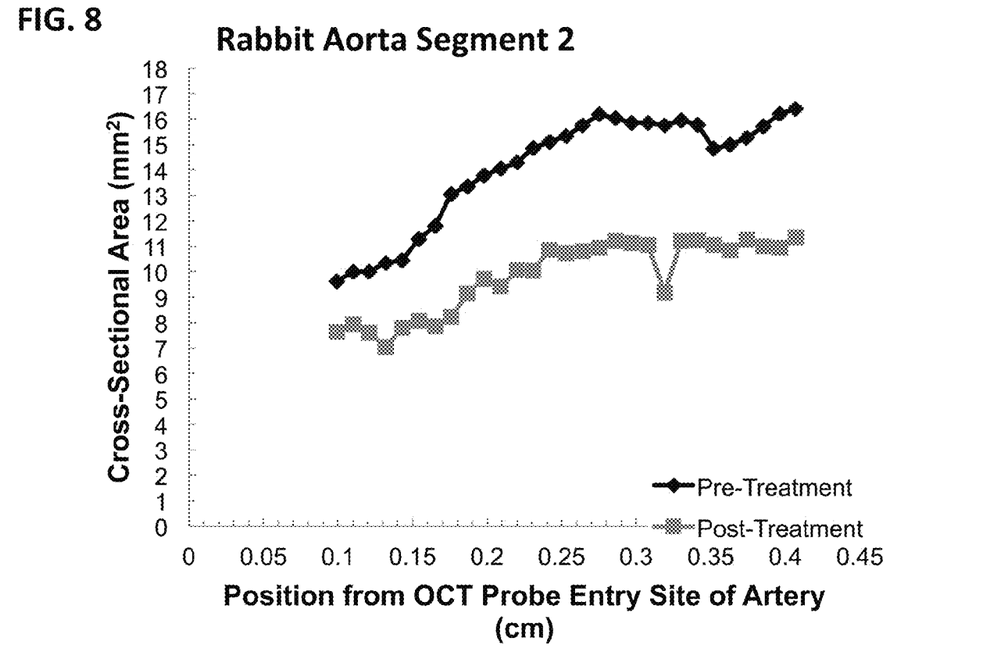
FIG. 8 shows cross-sectional area of the arterial lumen at each position from the OCT probe entry site of Aorta Specimen #2 showing both the pre-treatment and post-treatment OCT measurements.

An initial mass of 0.2 g was measured for of Aorta Specimen #2. Over the course of the three-hour control test, the flow rate entering this aorta specimen remained constant at 2.55 mL/s+/−0.02 mL/s. No significant change in flow rate was observed throughout the entire control test as shown in FIG. 8. After the control test was completed, Aorta Specimen #2 was removed from the system, dried, and weighed again. It was determined at this stage of the experiment that the mass of the specimen was virtually the same at 0.2 g.

Figure 9:
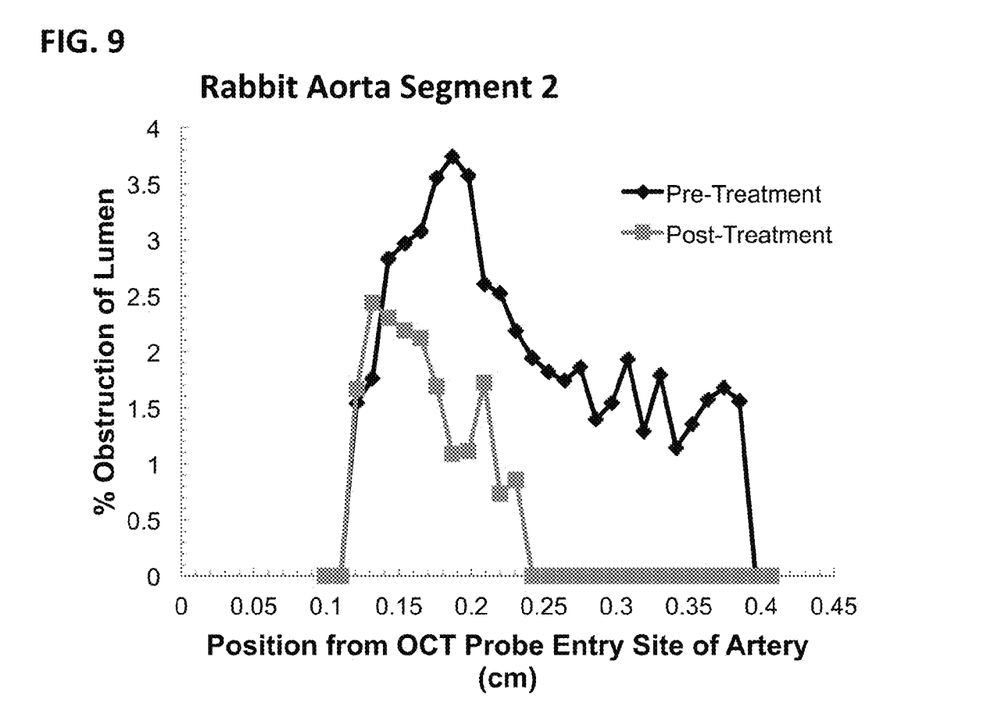
FIG. 9 shows percent obstruction of the lumen caused by the plaque deposit at each position from the OCT probe entry site of Aorta Specimen #2 showing both pre-treatment and post-treatment OCT measurements.

The AMF treatment test for Aorta Specimen #2 proceeded in a manner similar to that for Aorta Specimen #1. Over the course of the first 600 s, flow rate increased from 2.55 mL/s to 2.62 mL/s+/−0.02 mL/s. During the next 2400 s, the flow rate continued to increase until it eventually plateaued at 2.65 mL/s and remained at this flow rate for the remainder of the three hour test. The flow rate data for this test can be seen in FIG. 9. Once the AMF treatment test was completed, Aorta Specimen #2 was removed from the system, dried, and weighed for a third time, exhibiting a new lower mass of 0.12 g indicating a mass reduction of approximately 40%.

Neither aorta segment exhibited any external changes under the control, non-magnetic, conditions. Both specimens began the AMF treatment portion of the experiment exhibiting the same flow resistance as during the entirety of the control test. Thus, the switch to the AMF treatment flow path did not appear to interfere with the overall flow through the aorta segments. Both aorta segments also exhibited a drop in flow resistance, apparently due to plaque removal, during the initial stages of the AMF treatment portion of their experiments. For Aorta Specimen #1, the flow rate increased from 2.20 mL/s to 2.23 mL/s (+/−0.01 mL/s) or about 1.5%. The flow rate for Aorta Specimen #2 increased from 2.55 mL/s to 2.65 mL/s or about 5%. This result is consistent with the 40% mass reduction determined for Aorta Specimen #2 after the AMF treatment portion of the experiment.

OCT Images: OCT images were obtained of the interior of Aorta Specimen #2 both before and after the AMF treatment. For each OCT session, 135 frames of OCT images were obtained and analyzed using the digital image analysis tool, ImageJ (National Institutes of Health, Bethesda, MD), to measure the cross-sectional area of the arterial lumen as well as the atherosclerosis, or calcified plaque deposit, in each frame. Both measurements in each image were taken five times and averaged. The same plaque deposit was identified in frames 11 to 35 in the pre-treatment images and frames 25-35 in the post-treatment images. The appearance of this plaque deposit in 14 fewer frames after the AMF treatment indicates that a significant amount of plaque was removed. The percent area of arterial lumen obstruction due to the plaque deposit was also calculated. Frame 17 in the pre-treatment images displayed the largest percent area obstructed due to the plaque deposit at 3.74%. This frame is 0.187 cm from the end of Aorta Specimen #2 through which the OCT probe entered. The largest percent obstruction due to the plaque deposit in the post-treatment images was calculated to be 2.45% in frame 26, which was 0.132 cm from the OCT probe entry site of Aorta Specimen #2. This post-treatment maximum percent obstruction due to the plaque deposit indicates a 34.9% decrease in flow blockage.

CONCLUSIONS

An alternating magnetic field (AMF) device was used to treat Ringer's solution passing through a pair of previously formaldehyde preserved, plaque-lined rabbit aorta specimens in a closed-loop test for three hours, after a three-hour control exposure to the same solution and flow rate without AMF treatment. The pressure entering the aorta specimens was held constant and the reduction of plaque was measured by observing the changes in flow rate. For one aorta specimen, plaque reduction was also indicated by mass measurements and with pre-treatment and post-treatment OCT images of the interior of the aorta specimen. Over the course of the three-hour control test for both aorta specimens, no noticeable fluctuation in flow rate was observed. By contrast, both aorta specimens displayed a measurable increase in flow rate during the early stages of the 3 hour AMF treatment indicating a significant reduction in plaque. Mass measurements of Aorta Specimen #2 were made before the control test, after the control test, and after the AMF treatment. A negligible change in mass was seen after the control test but a 40% decrease in mass was recorded after the AMF treatment. A pre- and post-treatment comparison of OCT images of the interior of Aorta Specimen #2 revealed that the maximum percent area of the arterial passage obstructed by the plaque deposit was reduced by 34.9%. Thus, the present AMF treatment has exhibited significant potential for the dissolution of arterial plaque deposits in a rabbit model.

The disclosures of the following U.S. patents are incorporated in their entirety by reference herein: U.S. Pat. Nos. 7,632,400; 7,803,272; 7,914,677.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An alternating magnetic field (AMF) system (100) for producing nanobubbles comprising a pipe (110) with an enclosed core (120) mounted within the pipe, the core (120) extends along a length of the pipe (11) while allowing a liquid to flow through the pipe (110) and around the core (120) without entering the core (120), wherein a plurality of magnets (130) is housed in the core (120) oriented north end-to-north end and south end-to-south end, the magnets (130) expose the liquid to an alternating magnetic field, wherein the core (120) is shaped such that the liquid flows straight through the pipe (110), wherein a ratio of an outer diameter of the enclosed core (120) and an inner diameter of the pipe (110) is 1:3 to 35:64.

2. The system of claim 1, wherein the magnets comprise neodymium magnets.

3. The system of claim 1, wherein the magnets comprise a combination of two or more different types of magnets.

4. The system of claim 1, wherein the nanobubbles comprise oxygen bubbles.

5. The system of claim 1, wherein the liquid comprises calcium, carbonate, ions that can produce calcium bearing compounds, sodium chloride, selenium ions, or a combination thereof.

6. The system of claim 1, wherein a ratio of an outer diameter of the enclosed core (120) and an inner diameter of the pipe (110) is 35:64.

7. A method of producing nanobubbles, said method comprising:
    subjecting a solution to an alternating magnetic field (AMF) system comprising:
    a pipe (110) with an enclosed core (120) mounted within the pipe, the core (120) extends along a length of the pipe (110) while allowing the solution to flow through the pipe (110) and around the core (120) without entering the core (120), wherein a plurality of magnets (130) is housed in the core (120) oriented north end-to-north end and south end-to-south end, the magnets (130) expose the solution to an alternating magnetic field;
    wherein the core (120) is shaped such that the liquid flows straight through the pipe (110), wherein a ratio of an outer diameter of the enclosed core (120) and an inner diameter of the pipe (110) is 1:3 to 35:64;
    wherein the AMF system destabilizes gas molecules having been dissolved in the solution to precipitate nanobubbles comprising the gas molecules.

8. The method of claim 7, wherein the magnets comprise neodymium magnets.

9. The method of claim 7, wherein the magnets comprise a combination of two or more different types of magnets.

10. The method of claim 7, wherein the gas molecules comprise oxygen molecules.

11. The method of claim 7, wherein the solution comprises calcium.

12. The method of claim 7, wherein the solution comprises carbonate.

13. The method of claim 7, wherein the solution comprises ions that can produce calcium bearing compounds.

14. The method of claim 7, wherein the solution comprises sodium chloride.

15. The method of claim 7, wherein the solution comprises selenium ions.

16. The method of claim 7, wherein a ratio of an outer diameter of the enclosed core (120) and an inner diameter of the pipe (110) is 35:64.

17. A method of reducing fouling or corrosion in a tube or pipe system with flowing liquid, said method comprising:
    subjecting a solution to an alternating magnetic field (AMF) system to produce nanobubbles in the solution, the AMF system comprising:
    a pipe (110) with an enclosed core (120) mounted within the pipe, the core (120) extends along a length of the pipe (110) while allowing the solution to flow through the pipe (110) and around the core (120) without entering the core (120), wherein a plurality of magnets (130) is housed in the core (120) oriented north end-to-north end and south end-to-south end, the magnets (130) expose the solution to an alternating magnetic field; wherein the AMF system produces nanobubbles in the solution; wherein the core (120) is shaped such that the liquid flows straight through the pipe (110), wherein a ratio of an outer diameter of the enclosed core (120) and an inner diameter of the pipe (110) is 1:3 to 35:64; and
    introducing the nanobubbles of the solution to the liquid in the tube or pipe system, wherein the nanobubbles bind or cluster nanoparticles so the nanoparticles do not foul or corrode the tube or pipe system or induce the dissolution of larger solids in the liquid.

18. The method of claim 17, wherein the magnets comprise neodymium magnets.

19. The method of claim 17, wherein the magnets comprise a combination of two or more different types of magnets.

20. The method of claim 17, wherein a ratio of an outer diameter of the enclosed core (120) and an inner diameter of the pipe (110) is 35:64.

* * * * *